United States Patent

Brun et al.

[11] Patent Number: 5,834,364
[45] Date of Patent: Nov. 10, 1998

[54] METHOD OF IMPLEMENTING OF A REFERENCE SAMPLE FOR USE IN A DEVICE FOR CHARACTERIZING IMPLANTED DOSES

[75] Inventors: Alain Brun, Vif; Serge Lombard, Reaumont, both of France

[73] Assignee: SGS-Thomson Microelectronics, S.A., Gentilly, France

[21] Appl. No.: 770,791

[22] Filed: Dec. 20, 1996

[30] Foreign Application Priority Data

Dec. 20, 1995 [FR] France ................................. 95 15510

[51] Int. Cl.$^6$ .................................................. H01L 21/425
[52] U.S. Cl. ............................................. 438/527; 438/946
[58] Field of Search ............................. 438/946, 17, 527, 438/545

[56] References Cited

U.S. PATENT DOCUMENTS

| | | | |
|---|---|---|---|
| 4,257,825 | 3/1981 | Schaumburg | 148/1.5 |
| 4,584,027 | 4/1986 | Metz, Jr. et al. | 438/527 |
| 4,818,721 | 4/1989 | Wang | 437/22 |
| 4,854,710 | 8/1989 | Opsal et al. | 356/432 |
| 4,952,063 | 8/1990 | Opsal et al. | 356/432 |
| 4,956,698 | 9/1990 | Wang | 357/91 |
| 5,042,952 | 8/1991 | Opsal et al. | 356/432 |
| 5,130,271 | 7/1992 | Migita | 438/527 |

*Primary Examiner*—Brian Dutton
*Attorney, Agent, or Firm*—David V. Carlson; Robert E. Mates; Seed and Berry LLP

[57] ABSTRACT

A reference sample for the calibration of a device for characterizing doses implanted on a wafer, consisting in defining a succession of at least two parallel strips on the wafer. The reference sample is produced by depositing a first implant mask on the wafer according to a pattern leaving a first strip accessible, performing a first ionic implant of a first dose, removing the first implant mask and depositing a second implant mask on the wafer according to a pattern leaving accessible the first strip as well as a second contiguous strip, performing a second ionic implant of a second dose, and removing the second implant mask.

19 Claims, 2 Drawing Sheets

METHOD OF IMPLEMENTING OF A REFERENCE SAMPLE FOR USE IN A DEVICE FOR CHARACTERIZING IMPLANTED DOSES

BACKGROUND OF THE PRESENT INVENTION

1. Field of the Present Invention

The present invention relates to a method for characterizing doses implanted by ionic implantation on a wafer by means of a measuring device using a laser for thermally exciting the wafer. The present invention more specifically applies to calibrating the measuring device by means of reference samples.

2. Discussion of the Related Art

In a wafer production process using an implant and/or layer depositions, for example, the production of wafers in micro-electronics, a characterization of the doses implanted is performed to ensure that the required doses have been implanted. This characterization enables, for example, the adjustment of an ionic implant device used in the process. The use of a measuring device for characterizing implanted doses including an excitation laser is known. Such a device is called a thermal wave characterization device and the method is generally preferred to other prior techniques (for example, measuring the resistivity of an implanted layer by means of a so-called "four-point" probe) because the wafer does not deteriorate during the measurement. A thermal wave characterization device is known under trade name Thermaprobe®, sold by Thermawave.

Such a thermal wave characterization device uses two lasers, the beams of which are combined. A first, pulsed, excitation laser is meant to locally heat a point of a wafer to be characterized. Between two pulses, the heat generated at the point involved on the wafer is discharged by "thermal waves" characteristic of this point and of its environment. The thermal wave characterization device analyzes, between the two pulses, a reflected beam of a second continuous measurement laser illuminating the same point on the wafer. The intensity variations of the reflected beam are an image of the above-mentioned thermal waves since the reflectance of a surface depends on its temperature. Now, these thermal waves depend on three characteristic parameters of the implanted layer: the doping quantity, the energy of the ionic bombardment, and the type of impurities which disturb the crystal lattice. A survey of an entire wafer is performed by moving the wafer in two perpendicular directions in order to obtain a scan of the whole wafer by the laser beams. A complete characterization of the wafer that enables detection and location of the defects of the implanted layers is thus obtained.

As for any measuring device, the thermal wave characterization device must be calibrated periodically to enable a correction of possible operating drifts in the device. For this purpose, reference samples are generally used. Conventionally, several reference samples are implemented by means of several wafers having undergone ionic implants of different doses produced under identical bombardment power. A reference value of a signal issued by the thermal wave characterization device is associated with each wafer. The calibration of the device is performed by successively introducing the reference samples in the device and by scanning each reference sample.

A disadvantage of the conventional calibration method is that it requires several reference samples to be successively surveyed by the thermal wave characterization device to calibrate said device. If a more accurate calibration of the device is desired, then more reference samples must be surveyed by the device. Another disadvantage of the conventional calibration method is that the device cannot be calibrated while the device is being used to characterize wafers produced on a production line. Thus, it is necessary to stop the wafer production process to perform the calibration of the device.

SUMMARY OF THE PRESENT INVENTION

The present embodiment of the invention aims at overcoming the above-mentioned disadvantages by means of a sample which allows a calibration of the measuring device in its entire measurement range.

An embodiment of the invention also aims at enabling a calibration of the measuring device without it being necessary to interrupt the actual wafer characterization process on a production line.

To achieve these objects, an embodiment of the invention provides a method for manufacturing a reference sample for the calibration of a thermal wave characterization device characterizing doses implanted on a wafer consisting in defining a succession of at least two parallel strips on the wafer; depositing a first implant mask on the wafer according to a pattern leaving a first strip accessible; performing a first ionic implant of a first dose; removing the first implant mask and depositing a second implant mask on the wafer according to a pattern leaving accessible the first strip, as well as a second contiguous strip; performing a second ionic implant of a second dose; and removing the second implant mask.

According to an embodiment of the present invention, the reference sample receives at least one high temperature anneal. According to an embodiment of the present invention, the reference sample is characterized by means of the above-mentioned device to obtain a series of at least two reference values associated with the reference sample. According to an embodiment of the present invention, the ionic implants are all performed with identical bombardment power.

An embodiment of the invention also provides a reference sample of a device for characterizing doses implanted on a wafer of the type issuing a signal responsive to an excitation of the wafer by a laser beam, including a succession of at least two parallel strips having different implanted doses.

According to an embodiment of the present invention, the reference sample includes at least three parallel strips, and the doping doses decrease from one strip to another from a highly implanted first strip to a lightly implanted last strip.

An embodiment of the invention also provides a thermal wave characterization device for characterizing doses implanted on a wafer while the wafer is supported by a carriage which is mobile in a plane perpendicular to a laser beam. Proximate to the surface in which the wafer is inscribed is a sample carrier which is accessible to the laser beam during a displacement of the carriage, the sample carrier being meant to receive at least one reference sample including a succession of at least two parallel strips having different implanted doses. According to an embodiment of the present invention, the sample carrier constitutes a support of a chip for the automatic adjustment of the reflectivity of a continuous laser.

A method for automatically calibrating a thermal wave characterization device according to an embodiment of the present invention consists of placing a reference sample on the sample carrier; bringing the mobile carriage to a position where a first, pulsed, laser excites one point on a first strip of the reference sample; measuring the reflectance of the surface of this point by means of a second continuous laser; moving the carriage in a direction perpendicular to the strip to obtain a measurement value associated with a second strip; moving the carriage to obtain measurement values associated with a succeeding number of strips; and calibrating the device according to the deviation between the values measured and the reference values of the reference sample.

These objects, features and advantages, as well as others, of the present invention will be discussed in detail in the following description of specific embodiments, taken in conjunction with the following drawings, but not limited by them.

BRIEF DESCRIPTION OF THE DRAWINGS

For clarity, the same components have been referred to by the same reference numerals in the different drawings. For clarity still, the representations of the drawings are not to scale.

DETAILED DESCRIPTION

A characteristic of the present invention is to enable the implementation of a single reference sample to which are associated several values of a signal issued by a thermal wave characterization device, "thermal waves", are associated, enabling the characterization of doses implanted on a wafer, for example made of silicon. For this purpose, an embodiment of the present invention provides at least two successive ionic implants on a same silicon layer.

Figure 1A:
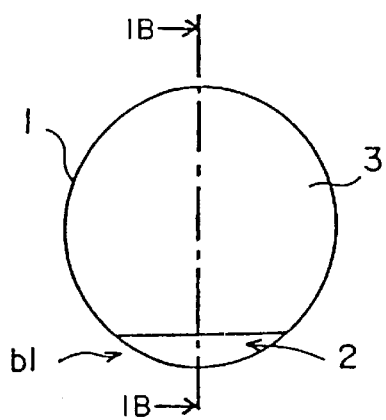
FIGS. 1A and 1B are, respectively, a plane view and a cross-sectional view of a wafer during a first phase of a method of an implementation mode of a reference sample according to an embodiment of the present invention.
Figure 1B:
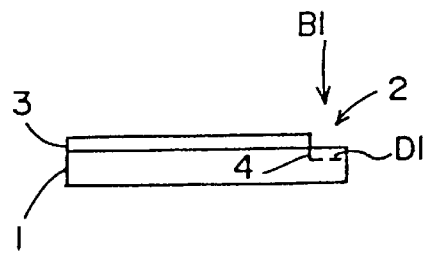
Figure 2A:
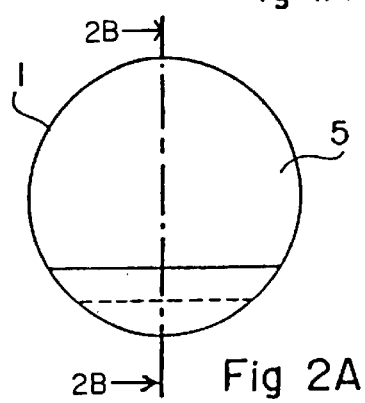
FIGS. 2A and 2B are, respectively, a plane view and a cross-sectional view of the wafer shown in FIGS. 1A and 1B during a second phase of the method according to an embodiment of the present invention.
Figure 2B:
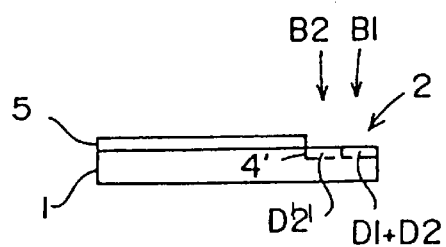
Figure 3A:
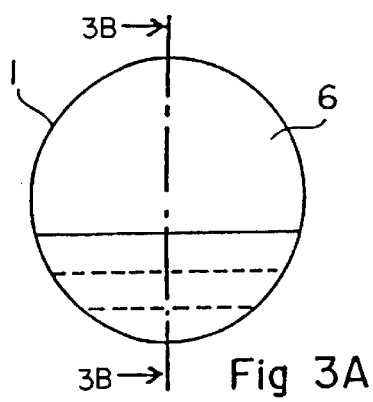
FIGS. 3A and 3B are, respectively, a plane view and a cross-sectional view of the wafer shown in FIGS. 2A and 2B during a third phase of the method according to an embodiment of the present invention.
Figure 3B:
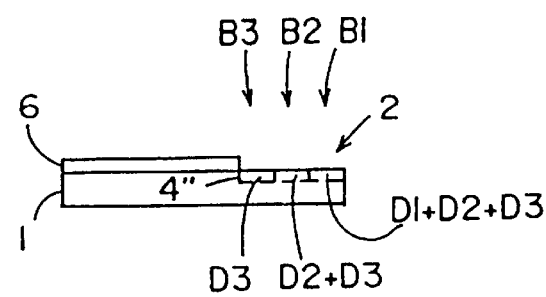

FIGS. 1A to 3B illustrate three successive ionic implants of a silicon wafer 1 meant to constitute a reference sample according to an embodiment of the present invention. FIGS. 1A, 2A and 3A are plane views of the silicon wafer 1 and FIGS. 1B, 2B and 3B are cross-sectional views following the lines B–B' of the FIGS. 1A, 2A and 3A, respectively.

During a first phase of the method according to the embodiment of the present invention (FIGS. 1A and 1B), a first implant mask 3 of an upper surface 2 of the wafer 1 is first deposited, according to a pattern which leaves accessible a first strip B1 perpendicular to a diametric direction of the wafer 1, a longitudinal edge of the first strip B1 being defined by a portion of the circumference of the wafer 1. The first implant mask 3 is, for example, made by a photolithographic resist layer. A first ionic implant of the wafer 1, during which only the unmasked region, that is, first strip B1 will be implanted, is then performed. An implanted layer 4 is thus formed on the first strip B1 with a first doping dose D1.

After removing the first implant mask 3, a second implant mask 5 is made during a second phase of the method according to the embodiment of the present invention (FIGS. 2A and 2B). The second implant mask 5 is made in the same way as the first implant mask 3 of the preceding phase but according to a pattern which leaves accessible, besides the first strip B1, a second strip B2 parallel and contiguous to the first strip B1. A second ionic implant is then performed on the wafer 1. Preferably, the second ionic implant is performed with the same ionic bombardment power as the first ionic implant. An implanted layer 4' is thus obtained, with its width corresponding to the cumulative widths of the first and second strips B1 and B2. The second strip B2 thus contains a doping dose D2 defined by the second ionic implant whereas the first strip B1 now contains a doping dose D1+D2, the implants being cumulative.

After removing the second implant mask 5, a third ionic implant according to a pattern defined by a third implant mask 6 (FIGS. 3A and 3B) is performed during a third phase of the method according to the embodiment of the present invention. The pattern of the third implant mask 6 is such that it leaves accessible a third strip B3 of the surface 2 of the wafer 1, the third strip B3 being parallel to the first and second strips B1 and B2 and contiguous to the second strip B2. An implanted layer 4" obtained after this third phase includes, respectively, the first, second, and third strips B1, B2 and B3, the respective implanted doses of which are D1+D2+D3, D2+D3 and D3.

Figure 4A:
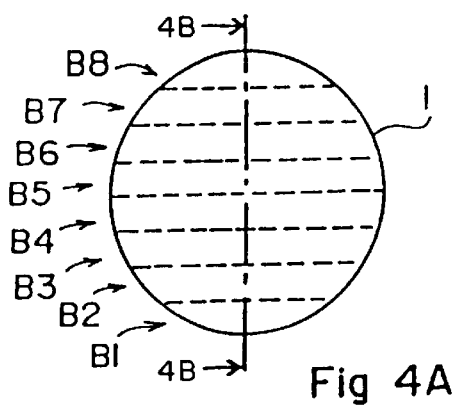
FIGS. 4A and 4B are, respectively, a plane view and a cross-sectional view of a first embodiment of a reference sample according to the present invention.
Figure 4B:
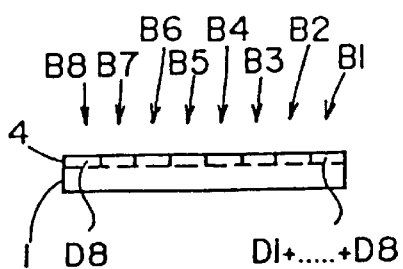

FIGS. 4A and 4B are, respectively, a plane view and a cross sectional view following the line B–B' of FIG. 4A, of a completed reference sample. In this example, the reference sample includes eight strips B1 to B8, each having different implanted doses. The first strip B1 is the most implanted strip, its doping dose corresponding to the addition of eight doses enumerated D1 to D8. The strip B8 is the least implanted strip, since it has only been submitted to the last implant with a dose D8.

A calibration of the thermal wave characterization device is performed by placing the reference sample in the place of a wafer. It is enough to perform a single scan in a direction perpendicular to the strips B1 to B8 of the reference sample to know all the dopant concentrations of the reference sample. The signals representative of the thermal waves obtained from the different strips of the reference sample enable a calibration of the thermal wave characterization device because the signals may be compared with the known dopant concentrations in the reference sample.

The doses implanted in each phase of the method according to the embodiment of the present invention are selected, preferably, so that the final doping doses applied to the different strips correspond to implant doses used in a production line associated with the thermal wave characterization device.

The number of strips of the reference sample according to the embodiment of the present invention depends on the number of reference values on which it is desired to base the calibration of the thermal wave characterization device. For example, the number of strips can correspond to the number of different implant doses used in the production line associated with the device.

An advantage of the embodiment of the present invention is that it considerably simplifies the calibration of a thermal wave characterization device. Especially, it enables an automatic calibration sequence when a reference sample such as the one shown in FIGS. 4A and 4B is introduced in the device. Preferably, all the strips B1 to B8 of the reference sample have the same width.

To avoid an instability of the implemented reference sample, the reference sample undergoes a high temperature annealing procedure at an approximate temperature of 1000° C. Indeed, in the absence of the annealing procedure, the reference values of the sample strips B1 to B8 would not be stable through time due to a reactivation of the crystal lattice. To determine the annealing time necessary to make the reference sample stable, short successive annealing procedures (of around 20 seconds each) could be, for example, performed until the signal issued by the device for each strip is identical after two successive annealings for each strip of the reference sample.

Figure 5:
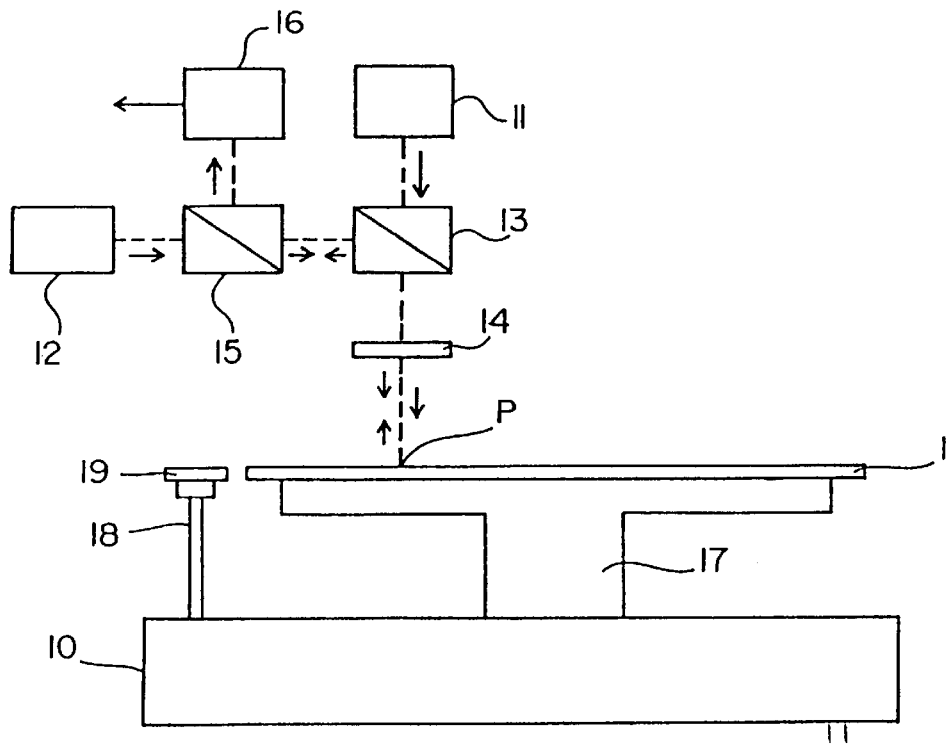
FIG. 5 is a side view of a thermal wave characterization device provided with a second embodiment of a reference sample according to the present invention.
Figure 6:
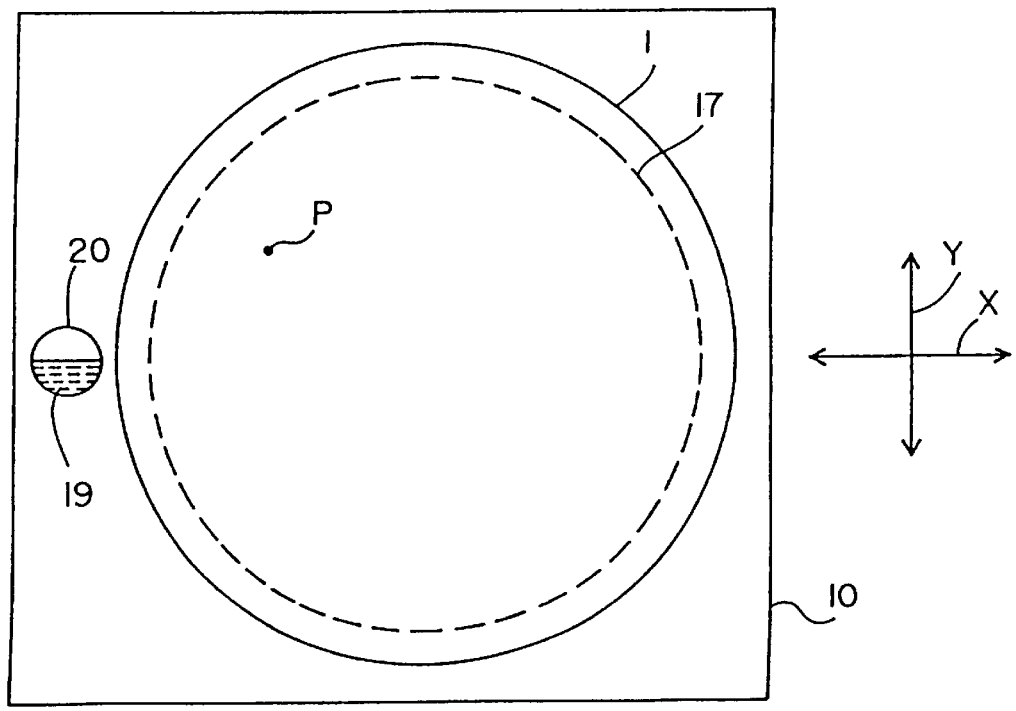
FIG. 6 is a plane view of a mobile carriage of a measuring device as shown in FIG. 5 according to an embodiment of the invention.

FIGS. 5 and 6 illustrate an example of application of a second embodiment of the invention. The Figures show a reference sample within a thermal wave characterization device. FIG. 5 is an elevational view of the device according to a second embodiment of the invention. FIG. 6 is a plane view of a mobile carriage 10 of the device shown in FIG. 5. For clarity, only the components necessary for the understanding of the present invention have been shown in FIGS. 5 and 6.

The operation of a thermal wave characterization device is conventional and will only very generally be described herein. The device includes two lasers 11 and 12. A first, pulsed, laser 11, for example an argon laser, heats a point P of the surface of a wafer 1 to be analyzed. Between two pulses of the laser 11, the heat generated at point P is transferred by the "thermal waves" characteristic of the heated point and of its environment. A second laser 12, continuous and with a low power, for example a helium-neon laser, illuminates the same point P. Its reflected beam is analyzed. With reference to FIG. 5, the beams of lasers 11 and 12 are combined by a combiner 13 and concentrated by a focusing lens 14 on the point P. The reflected beam of the laser 12 is sent back by the combiner 13 to a separator 15 and a detector 16, where the detector 16 provides an image of a thermal wave signal corresponding to the thermal waves emanating from the point P.

The thermal wave signal enables, notably, to locally detect inhomogeneities interruptions in the homogeneity of implanted doses, impurities other than the desired doping(s), or ruptures of the crystal lattice.

It should be noted that the thermal wave signal is independent from the nature of the implanted species. Thus, the calibration of the thermal wave characterization device according to the embodiment of the present invention is independent from the species implanted in the reference sample.

With reference to FIG. 5, the measuring device includes a mobile carriage 10 on which a wafer support 17 is mounted for receiving the wafer 1 to be characterized. The mobile carriage 10 is mobile in two perpendicular directions, symbolized by arrows X and Y in FIG. 6, to enable a scan of the surface of the wafer 1 by the thermal wave characterization device.

According to the embodiment of the present invention, the mobile carriage 10 also supports a sample carrier 18 for receiving at least one reference sample 19 implemented according to the second embodiment of the present invention. The sample carrier 18 is disposed proximate to the area where the wafer 1 to be characterized is inscribed. The reference sample 19 has a reduced size with respect to the size of the wafer 1. The reference sample 19 can be obtained by cutting out a chip with a small diameter (for example around 10×10 mm) from a silicon wafer which is submitted to the process described in relation to FIGS. 1 to 4. In this case, the width of the strips defined in the wafer used to implement the reference sample is adapted so that the whole range of implanted doses to be used is contained in the cut-out chip. An advantage of this embodiment is that it enables the reference sample to always be present in the thermal wave characterization device during the characterization of the wafers to be examined. It is thus possible to perform a calibration of the device without interrupting the characterization of the wafers manufactured on the production line associated with the device. It is for example provided to periodically calibrate the device between each wafer or between two batches of wafers in a production process.

Preferably and as shown in FIG. 6, the reference sample 19 is associated with a chip 20, generally made of platinum, provided on the thermal wave characterization device to calibrate the reflectivity of the laser 12. The existence of an area of the mobile carriage 10, the scanning of which is already provided by the control device (not shown) of the measuring device, is thus used, which simplifies the programming of the control device to perform the calibration according to the embodiment of the present invention. The adaptations of the control device, which is generally programmable, are within the abilities of those skilled in the art.

Of course, the present invention may have various alterations, modifications and improvements which will occur to those skilled in the art. Especially, the number of strips of the reference sample, be it for the first or the second embodiment described hereabove, can be modified according to the desired calibration of the thermal wave characterization device. Moreover, it should be noted that a reference sample according to an embodiment of the present invention can also be implemented by successive ionic implants of doses defined individually for each strip. In this case, each strip is implanted only once and the implant masks are adapted accordingly. Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A method for manufacturing a reference sample for a calibration of a device that characterizes doses implanted into a wafer, comprising:

defining at least first and second strips on a sample wafer;

depositing a first implant mask on the sample wafer according to a pattern that leaves the first strip uncovered by said first implant mask;

performing a first ionic implant of a first dose;

removing the first implant mask and depositing a second implant mask on the sample wafer according to a pattern that leaves the first strip and the second strip uncovered by said second implant mask;

performing a second ionic implant of a second dose; and removing the second implant mask.

2. The method of claim 1, further comprising the step of annealing the sample wafer.

3. The method of claim 2, further comprising the step of characterizing the sample wafer by the device to obtain a series of at least two reference values associated with the sample wafer.

4. The method of claim 2 wherein the step of defining at least first and second strips on a sample wafer comprises defining at least first and second strips which are parallel and contiguous on a sample wafer.

5. The method of claim 2 wherein the step of annealing the sample wafer comprises annealing the sample wafer at a temperature of approximately 1000° C.

6. The method of claim 1, further comprising the step of characterizing the sample wafer by the device to obtain a series of at least two reference values associated with the sample wafer.

7. The method of claim 1, further comprising the steps of:
bombarding the sample wafer to perform the first ionic implant at a first power; and
bombarding the sample wafer to perform the second ionic implant at a second power substantially identical to the first power.

8. The method of claim 1, further comprising the steps of:
defining a third strip on the sample wafer;
depositing a third implant mask on the sample wafer according to a pattern that leaves the first, second, and third strips uncovered by said third implant mask;
performing a third ionic implant of a third dose; and
removing the third implant mask.

9. A method for manufacturing a semiconductor sample comprising:
depositing a first mask onto a sample wafer;
processing the first mask such that the sample wafer is covered by the first mask except in a first region;
implanting ions into the first region;
removing said first mask from the sample wafer;
depositing a second mask onto the sample wafer;
processing the second mask such that the sample wafer is covered by the second mask except in said first region and in a second region;
implanting ions into the first region and the second region; and
removing said second mask from the sample wafer.

10. The method of claim 9, further comprising:
depositing a third mask onto the sample wafer;
processing the third mask such that the sample wafer is covered by the third mask except in said first and second regions, and in a third region;
implanting ions into the first, second, and third regions; and
removing said third mask from the sample wafer.

11. The method of claim 10 wherein the step of processing the second mask comprises processing the second mask such that the sample wafer is covered by the second mask except in said first region and in a second region contiguous to the first region and the step of processing the third mask comprises processing the third mask such that the sample wafer is covered by the third mask except in said first and second regions, and in a third region contiguous to the first and second regions.

12. The method of claim 10 wherein the steps of implanting ions into the first region, implanting ions into the first region and the second region, and implanting ions into the first, second, and third regions each further comprise the step of implanting the ions at a substantially constant power from a substantially constant ion source.

13. The method of claim 10, further comprising the step of annealing the sample wafer at approximately 1000° C.

14. The method of claim 10, further comprising the steps of annealing the sample wafer repeatedly until a thermal wave characterization of the sample wafer does not change with further annealing steps.

15. The method of claim 10 wherein the steps of depositing a first mask, depositing a second mask, and depositing a third mask each comprise the steps of:
depositing photoresist onto the sample wafer; and
exposing the photoresist.

16. A method for manufacturing a reference sample in a semiconductor wafer, comprising:
masking a first portion of a wafer, leaving an unmasked portion of the wafer and a masked portion of the wafer;
implanting ions into the unmasked portion of the wafer to form a first implanted region;
removing the mask;
masking a second portion of the wafer, leaving unmasked the first implanted region and a further portion of the wafer;
implanting ions into the first implanted region and the further portion to form a second implanted region; and
removing the mask.

17. The method of claim 16, further comprising:
masking a third portion of the wafer, leaving unmasked the second implanted region and a further portion of the wafer;
implanting ions into the second implanted region and the further portion; and
removing the mask.

18. The method of claim 17, further comprising the step of characterizing the wafer using thermal waves to generate a profile of ion concentration in the wafer.

19. The method of claim 18, further comprising the steps of annealing the wafer repeatedly at approximately 1000° C. such that the characterization of the wafer does not change with further annealing steps.

* * * * *